United States Patent [19]

Peake et al.

[11] Patent Number: 4,584,318
[45] Date of Patent: Apr. 22, 1986

[54] NEMATICIDAL SALICYLALDEHYDE DERIVATIVES

[75] Inventors: Clinton J. Peake, Trenton; Carmine P. DiSanzo, Lawrenceville, both of N.J.; John F. Engel, Washington Crossing, Pa.

[73] Assignee: FMC Corporation, Philadelphia, Pa.

[21] Appl. No.: 505,606

[22] Filed: Jun. 20, 1983

Related U.S. Application Data

[63] Continuation-in-part of Ser. No. 273,899, Jun. 15, 1981, abandoned.

[51] Int. Cl.$^4$ .................... C07C 69/00; A01N 37/02; A01N 37/06
[52] U.S. Cl. ................... 514/546; 514/488; 514/490; 514/534; 514/535; 514/549; 514/550; 514/551; 556/422; 556/486; 560/20; 560/23; 560/32; 560/65; 560/73; 560/108; 560/109; 560/133; 560/136; 560/138; 560/142; 564/256; 558/234
[58] Field of Search ............ 560/20, 32, 133, 136, 560/73, 108, 109, 138, 142, 23, 65; 424/184, 300, 308, 311, 314, 327, 309; 260/455 A; 564/256; 556/422, 486; 514/546, 550, 551

[56] References Cited

U.S. PATENT DOCUMENTS 2,712,031 6/1955 Huffman ........................ 564/220
3,129,136 4/1964 Mayer ............................. 424/333
4,347,372 8/1982 Föry et al. ...................... 560/142

FOREIGN PATENT DOCUMENTS 0012158  6/1980  European Pat. Off. ............ 564/256
0094177 12/1972  Fed. Rep. of Germany .
3018670 11/1981  Fed. Rep. of Germany ... 260/455 A
47/17994  5/1972  Japan ................................. 424/300
55/59159  5/1980  Japan .
68/02699 11/1968  South Africa .
1096037 12/1967  United Kingdom ................. 564/256

OTHER PUBLICATIONS

*Pesticide Biochemistry and Physiology*, vol. 4, pp. 77–85 (1974), Lee et al.

Primary Examiner—Natalie Trousof
Assistant Examiner—Patricia M. Scott
Attorney, Agent, or Firm—H. H. Young, Jr.; H. R. Ertelt

[57] ABSTRACT

A method is described for the control of nematodes in agricultural crops which comprises applying to the situs of infestation of a nematicidal composition containing as active ingredient a compound of the formula

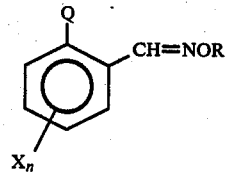

wherein Q is hydroxy, carbamoyloxy, or acyloxy, R is alkyl, alkenyl, alkynyl, X is halogen or methyl, n is 1 or 2. Preparation of active ingredient compounds is described, and nematicidal utility of compositions is exemplified.

13 Claims, No Drawings

NEMATICIDAL SALICYLALDEHYDE DERIVATIVES

This application is a continuation-in-part of application Ser. No. 273,899, filed June 15, 1981 abandoned.

This invention relates to a composition and a method for controlling nematodes and to novel nematicidal compounds. More particularly, the invention relates to derivatives of salicylaldoxime useful as a nematicide for agricultural crops.

Aromatic aldehydes and their imine derivatives have been reported to exhibit anthelmintic activity. Halogenated salicylaldehydes have been found to exhibit activity against ascarids (intestinal round worms) and insects. U.S. Pat. No. 3,129,136 (1964) claims nematode control with 2-chloro-3-hydroxy-4-nitrobenzaldehyde. East German Pat. No. 94,177 (1972) discloses aldoximes, including 4-chloro-2-[(hydroxyimino)methyl]phenol and 4-chlorobenzaldoxime as nematicides. Phenyl N-methylcarbamates with alkoxyiminomethyl moieties in the ortho position were reported by Lee, Sanborn and Metcalf (Pesticide Biochemistry and Physiology 4, 77-85 (1974)) to be insecticides.

No reference has been found which discloses or suggests the activity of the derivatives of salicylaldoxime against soil nematodes which is now disclosed for the first time.

The present invention comprises a method for controlling nematodes in agricultural crops by applying to the situs of infestation a nematicidally effective amount of a compound of the formula

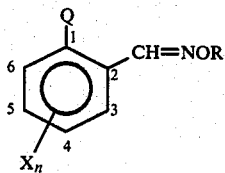

wherein
Q is —OH,

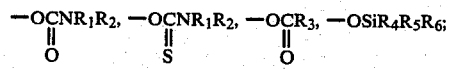

R is alkyl, alkenyl, alkynyl, straight, branched, or cyclic, containing up to eight carbon atoms;
$R_1$ is $C_1$-$C_4$ alkyl, phenyl;
$R_2$ is H, $C_1$-$C_4$ alkyl;
$R_3$ is alkyl, alkenyl, alkynyl, straight or branched, containing up to eight carbon atoms, or phenyl, and $R_3$ may be optionally substituted with nitro, halogen, alkoxy;
$R_4$, $R_5$, $R_6$ are $C_1$-$C_4$ alkyl, which may be the same or different;
X is fluorine, chlorine, bromine, methyl in the 3-, 4-, or 5-position which may be the same or different when n is 2, and with the proviso that X is not methyl when n is 1;
n is 1 or 2.

It is contemplated that R may also be alkoxyalkyl, alkoxyalkoxyalkyl, dialkylaminoalkyl, or hydroxyalkyl, and that R may be optionally substituted with halogen or cyano. It is contemplated that $R_1$ as phenyl may be optionally substituted. It is further contemplated that $R_3$ may comprise an alicyclic or heterocyclic group, optionally substituted with halogen, cyano, alkoxy, nitro, and that alkyl, alkenyl, alkynyl, straight or branched $R_3$ substituents may be optionally substituted with halogen, cyano, alkoxy.

Preferred compounds for use in the method of the invention include those in which Q is —OH,

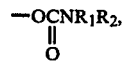

and

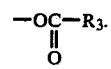

In especially preferred compounds for use in the method of the invention, Q is —OH and

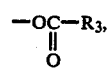

R is $C_2$-$C_6$ alkyl, $C_3$-$C_5$ alkenyl, $C_3$-$C_5$ alkynyl, X is in the 4-position when n is 1, and is in the 3,4- or 4,5-positions when n is 2.

The nematicidal compositions of this invention are those in which the active ingredient is present in admixture with an agriculturally acceptable carrier, diluent, or extender.

The nematicides of this invention, like most agricultural chemicals, are generally not applied full strength, but are formulated with agriculturally acceptable carriers normally employed for facilitating the dispersion of active ingredients, various additives, and optionally with other active ingredients, recognizing the accepted fact that the formulation and mode of application of a toxicant may affect the activity of the material. The present compounds may be applied, for example, to the soil in which nematode control is desired as granules or powders or liquids, the choice of application varying, of course, with the nematode species and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the nematicides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 45 μm (No. 325, U.S.A. Standard Sieve Series). In most cases, the active ingredient will be present in dust formulations at a concentration in the range of 1 to 15%, and occasionally from 1% to about 30%, the balance of the composition typically being agriculturally acceptable carrier or diluent.

Wettable powders, also useful formulations for these nematicides, are in the form of finely divided particles which disperse readily in water or other liquid vehicles. The wettable powder is ultimately applied to the soil or plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp<100° C.) are suitably formulated in the concentration range of 5 to 50% by weight, usually from 10 to 30%; high melting solids (mp>100° C.) are formulated in the range of 5 to 95% by weight, usually 50 to 85%. An agriculturally acceptable carrier or diluent, frequently including a small amount of a surfactant to facilitate wetting, dispersion and suspension, accounts for the balance of the formulation.

Granules are admixtures of the active ingredients with solids of particle sizes generally in the range of 4.75 mm to 150 μm (No. 4 to No. 100, U.S.A. Standard Sieve Series). Granular formulations may employ hard core materials such as sands and other silicates, mineral carbonates, sulfates or phosphates and the like, or porous cores such as attapulgite clays, fuller's earth, kieselguhr, chalk, diatomaceous earths, ground corn cobs, wood dusts and the like. Impregnating or binding agents such as aliphatic and aromatic petroleum solvents, alcohols, ethers, ketones, esters, vegetable oils, polyvinyl acetates, polyvinyl alcohols, dextrins, sugars and the like are commonly used to aid in coating or impregnating the solid carriers with the active ingredient. Emulsifying agents, wetting agents, dispersing agents, and other additives known in the art may also be added.

A typical granular formulation may suitably contain from about 1% to about 50% by weight active ingredient and 99% to 50% by weight of inert materials.

Microencapsulated or other controlled release formulations may also be used with nematicides of this invention for control of nematodes.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5 to 5% being surfactant and liquid carrier.

Flowables are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the nematicidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the nematicide in use dilution is normally in the range of about 2% to about 0.1%. Many variations of spraying, dusting, soil-incorporated, and controlled or slow release compositions in the art may be used by substituting or adding a compound of this invention into compositions known or apparent to the art.

Nematicidal compositions may be formulated and applied with other suitable active ingredients, including other nematicides, insecticides, acaricides, fungicides, plant regulators, herbicides, fertilizers, or with synergists.

In applying the foregoing chemicals, whether alone or with other agricultural chemicals, an effective nematicidal amount must be applied. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare. Trees and vines for example may require at least 5 kg/hectare whereas annuals such as corn may require considerably lower rates of application, for example 1 to 5 kg/hectare.

Preparation of the nematicidal compounds and of intermediates from which they are prepared is described in the following examples. In the descriptions which follow, all temperatures are in degrees Celsius, and reduced pressures are shown in Pascals (Pa); pressures not so designated are pressures normally attainable using a water aspirator.

EXAMPLE 1

4-Chloro-2-[(2-propynoxyimino)methyl]phenol

Step 1. Synthesis of N-2-propynoxyphthalimide as an intermediate

A stirred solution of 163.1 grams (1.00 mole) of N-hydroxyphthalimide, 448.0 grams (3.74 moles) of 2-propynyl bromide, 72.0 grams (0.52 mole) of potassium carbonate and 60.0 grams (0.82 mole) of dimethylformamide was heated under reflux for 16 hours. The reaction mixture containing a hardened solid was cooled. The solid was broken up by the addition of ethanol and stirring. The solid was collected by filtration and washed with additional ethanol, then with water until the washings were free of bromide ion when tested with silver ion. The solid was dried in a vacuum desiccator then recrystallized from hot ethanol to give 127.3 grams of N-2-propynoxyphthalimide; mp 146°–148.5°.

The ir spectrum was consistent with the assigned structure.

Step 2 Synthesis of 0-2-propynylhydroxylamine hydrochloride as an intermediate

A stirred mixture of 126.7 grams (0.63 mole) of N-2-propynoxyphthalimide (Step 1 product) and 148.4 ml of concentrated hydrochloric acid in 532.1 ml of glacial acetic acid was heated under reflux until complete solution was obtained (15 minutes). The reaction mixture was cooled to ambient temperature and a solid precipitate formed. The solid was collected by filtration; mp 208°–210°, decomposition, indicating the solid to be by-product phthalic acid (listed mp 208°, decomposition). The pH of the filtrate was adjusted to greater than 7 using aqueous 30% sodium hydroxide, while keeping the temperature of the filtrate near ambient temperature. The mixture was divided into two portions and each portion was extracted with four portions of 125 ml each of methylene chloride. The combined extracts were dried with sodium sulfate and filtered. The filtrate was placed in a reaction vessel equipped with a gas inlet tube and hydrogen chloride was bubbled into the solution while the vessel and contents were maintained at 10°–15°. A whitish-tan solid precipitated and was collected by filtration. The filtrate was treated with additional hydrogen chloride gas to collect additional solid. The procedure was repeated until no more solid precipitated. The combined solids were dried in a vacuum desiccator to give 26.8 grams of 0-2-propynylhydroxylamine hydrochloride; mp 153°–154°.

The ir spectrum was consistent with the assigned structure.

Step 3. Synthesis of 4-chloro-2-[(2-propynoxyimino)methyl]phenol

Solutions of 3.8 grams (0.35 mole) of 0-2-propynylhydroxylamine hydrochloride (step 2 product) in 35 ml of water and 1.2 grams (0.030 mole) of sodium hydroxide in 35 ml of water were added to 3.9 grams (0.025 mole) of 5-chlorosalicylaldehyde. Ethanol was added to the mixture until solution was obtained. The reaction mixture was heated on a steam bath for one hour, then cooled. The resultant solid precipitate was collected by filtration. The solid was recrystallized from hexane to give 2.6 grams of 4-chloro-2-[(2-propynoxyimino)methyl]phenol; mp 71°–73°.

The nmr and the ir spectra were consistent with the assigned structure.

Analysis Calc'd for $C_{10}H_8ClNO_2$: C 57.30; H 3.84; N 6.68. Found: C 57.34; H 4.12; N 6.41.

EXAMPLE 2

4-Chloro-2-[(2-propynoxyimino)methyl]phenylmethylcarbamate

A solution of 2.4 grams (0.011 mole) of 4-chloro-2-[(2-propynoxyimino)methyl]phenol (Example 1 product), 0.7 gram (0.013 mole) of methyl isocyanate and three drops of triethylamine in 50 ml of methylene chloride was stirred at ambient temperature for 16 hours. The reaction mixture was concentrated under reduced pressure to give a residual solid. The residue was recrystallized from toluene-hexane to give a solid; mp 97°–100°. The solid was slurried in hot water and collected by filtration. A second recrystallization from toluene-hexane gave 2.2 grams of 4-chloro-2-[(2-propynoxyimino)methyl]phenyl methylcarbamate; mp 99.5°–100.5°.

The nmr and the ir spectra were consistent with the assigned structure.

Analysis Calc'd for $C_{12}H_{11}ClN_2O_3$: C 54.05; H 4.16; N 10.50. Found: C 54.02; H 4.27; N 10.67.

EXAMPLE 3

4-Chloro-2-[(propoxyimino)methyl)]phenyl acetate

To a stirred solution of 6.4 grams (0.03 mole) of 4-chloro-2-[(propoxyimino)methyl]phenol (prepared in the manner of Example 1) in 50 ml of acetic anhydride was added in one portion 2.5 grams (0.03 mole) of sodium acetate. The reaction mixture was heated at 90°–100° for two hours, cooled to ambient temperature, and poured into 200 ml of ice-water. The mixture was stirred until the ice melted. A colorless oil separated and was extracted with portions of methylene chloride. The combined extracts were dried with sodium sulfate and filtered. The filtrate was concentrated under reduced pressure to a residual oil. The oil was distilled under reduced pressure to give 5.4 grams of 4-chloro-2-[(propoxyimino)methy]phenyl acetate; bp 95°–107°/3.333 Pa.

The nmr and the ir spectra were consistent with the assigned structure.

Analysis Calc'd for $C_{12}H_{14}ClNO_3$: C 56.37; H 5.52; N 5.48. Found: C 56.34; H 5.56; N 5.37.

The method of Example 1 was employed to prepare the following compounds in which Q is OH; the nmr and ir spectra were consistent with the assigned structures: EXAMPLE 4

5-Chloro-2-[(2-propynoxyimino)methyl]phenol mp 73°–76°; analysis calc'd: C 57.30, H 3.84, N 6.68; found: C 57.19, H 4.07, N 6.88.

EXAMPLE 5

4-Chloro-2-[(2-propenoxyimino)methyl]phenol mp 33.5°–34°; analysis calc'd: C 57.02, H 4.31, N 6.65; found: C 57.13, H 4.86, N 6.60.

EXAMPLE 6

2-[(3-Butenoxyimino)methyl]-4-chlorophenol mp 35.5°–36.5°; analysis calc'd: C 58.54, H 5.36, N 6.21; found: C 58.53, H 5.47, N 6.09.

EXAMPLE 7

4-Bromo-2-[(2-propynoxyimino)methyl]phenol mp 85°–87°; analysis calc'd: C 47.27, H 3.17, N 5.51; found: C 47.62, H 3.71, N 4.63.

EXAMPLE 8

4-Chloro-2-[(methoxyimino)methyl]phenol mp 65°–66°; analysis calc'd: C 51.77, H 4.34, N 7.55; found: C 51.78, H 4.61, N 7.78.

EXAMPLE 9

4-Chloro-2-[(ethoxyimino)methyl]phenol mp 35°–36°; analysis calc'd: C 54.15, H 5.15, N 7.02; found: C 54.41, H 4.77, N 6.94.

EXAMPLE 10

4-Bromo-2-[(methoxyimino)methyl]phenol mp 76.5°–78°; analysis calc'd: C 41.77, H 3.50, N 6.09; found: C 41.52, H 3.69, N 6.04.

EXAMPLE 11

4-Bromo-2-[(ethoxyimino)methyl]phenol mp 51°–53°; analysis calc'd: C 44.28, H 4.13, N 5.74; found: C 44.21, H 4.17, N 5.72.

EXAMPLE 12

4-Bromo-2-[(propoxyimino)methyl]phenol mp 31°; analysis calc'd: C 46.53, H 4.69, N 5.43; found: C 46.10, H 4.56, N 5.45.

EXAMPLE 13

4-Bromo-2-[(butoxyimino)methyl]phenol mp 42°–44°; analysis calc'd: C 48.55, H 5.18, N 5.15; found: C 48.32, H 5.36, N 5.12.

EXAMPLE 14

4-Chloro-2-[(propoxyimino)methyl]phenol bp 69°–72°/0.7 Pa; analysis calc'd: C 56.21, H 5.66, N 6.56; found: C 55.98, H 5.87, N 6.63.

EXAMPLE 15

4-Chloro-2-[(butoxyimino)methyl]phenol bp 86°–90°/0.7 Pa; analysis calc'd: C 58.03, H 6.19, N 6.15; found: C 56.91, H 6.15, N 6.40.

EXAMPLE 16

4-Chloro-2-[(1-methylethoxyimino)methyl]phenol mp 40°–80°; analysis calc'd: C 56.21, 5.66, N 6.56; found: C 55.96, H 5.55, N 6.29.

EXAMPLE 17

4-Chloro-2-[(2-methylpropoxyimino)methyl]phenol mp 35°–36°; analysis calc'd: C 58.03, H 6.20, N 6.15; found: C 58.24, H 6.11, N 5.82.

EXAMPLE 18

4-Chloro-2-[(3-methylbutoxyimino)methyl]phenol bp 104°–105°/1.3 Pa; analysis calc'd: C 59.63, H 6.67, N 5.79; found: C 59.98, H 6.56, N 5.69.

EXAMPLE 19

4-Chloro-2-[(1-methylpropoxyimino)methyl]phenol bp 87°–93°/2.0 Pa; analysis calc'd: C 58.03, H 6.19, N 6.15; found: C 58.18, H 5.96, N 6.16.

EXAMPLE 20

4-Fluoro-2-[(propoxyimino)methyl]phenol bp 50°/0.7 Pa; analysis calc'd: C 60.90, H 6.13, N 7.10; found: C 62.06, H 6.31, N 7.93.

EXAMPLE 21

3-Chloro-2-[(ethoxyimino)methyl]phenol oil.

EXAMPLE 22

5-Chloro-2-[(ethoxyimino)methyl]phenol mp 33°–34°; analysis calc'd: C 54.15, H 5.05, N 7.02; found: C 53.74, H 5.21, N 6.77.

EXAMPLE 23

2-[(2-Butenoxyimino)methyl]-4-chlorophenol mp 38.5°–39.5°; analysis calc'd: C 58.54, H 5.36, N 6.21; found: C 58.41, H 5.09, N 6.00.

EXAMPLE 24

4-Chloro-2-[(2-methyl-2-propenoxyimino)methyl]phenol bp 82°–85.5°/4 Pa; analysis calc'd: C 58.54, H 5.36, N 6.21; found: C 58.24, H 5.18, N 6.26.

EXAMPLE 25

4-Chloro-2-[(3-methyl-2-butenoxyimino)methyl]phenol mp 41.5°–42.5°; analysis calc'd: C 60.13, H 5.89, N 5.84; found: C 59.87, H 5.59, N 5.65.

EXAMPLE 26

4-Chloro-2-[(hexoxyimino)methyl]phenol bp 104°–112°/1.3 Pa; analysis calc'd: C 61.05, H 7.09, N 5.48; found: C 61.26, H 6.86, N 5.48.

EXAMPLE 27

4-Chloro-2-[(1-methyl-2-propynoxyimino)methyl]phenol mp 49.5°–50.5°; analysis calc'd: C 59.07, H 4.51, N 6.26; found: C 59.36, H 4.46, N 6.34.

Example 28

4-Chloro-2-[(methoxyimino)methyl]-3-methylphenol mp 66°–68°; analysis calc'd: C 54.15, H 5.05, N 7.02; found: C 54.35, H 5.12, N 6.87.

EXAMPLE 29

4-Chloro-2-[(methoxyimino)methyl]-5-methylphenol mp 75°–77°; analysis calc'd: C 54.15, H 5.05, N 7.02; found C 54.35, H 5.04, N 7.00.

EXAMPLE 30

Mixture of
4-chloro-2-[(methoxyimino)methyl]-5-methylphenol
and
4-chloro-2-[(methoxyimino)methyl]-3-methylphenol mp 41°–57°; analysis calc'd: C 54.15, H 5.05, N 7.02; found: C 54.42, H 5.02, N 6.68.

EXAMPLE 31

2-[(3-Butenoxyimino)methyl]-4-chloro-5-methylphenol mp 34°–35°; analysis calc'd: C 60.13, H 5.89, N 5.85; found: C 60.02, H 5.77, N 6.14.

EXAMPLE 32

Mixture of
4-chloro-5-methyl-2-[(propoxyimino)-methyl]phenol
and
4-chloro-3-methyl-2-[(propoxyimino)-methyl]phenol bp 81°/2 Pa; analysis calc'd: C 57.77, H 6.61, N 6.13; found: C 58.07, H 5.90, N 6.66.

EXAMPLE 33

4-Fluoro-2-[(methoxyimino)methyl]phenol mp 34°–35.5°; analysis calc'd: C 56.80, H 4.77, N 8.28; found: C 56.59, H 4.60, N 7.42.

EXAMPLE 34

2-[(Butoxyimino)methyl]-4-fluorophenol bp 73°–75°/10 Pa; analysis calc'd: C 62.55, H 6.68, N 6.63; found: C 62.60, H 7.72, N 6.81.

EXAMPLE 35

2-[(Cyclopropylmethoxyimino)methyl]-4-fluorophenol mp 44°–45.5°; analysis calc'd: C 63.15, H 5.78, N 6.69; found: C 63.43, H 6.05, N 6.72.

EXAMPLE 36

4-Fluoro-2-[(2-propynoxyimino)methyl]phenol mp 64°–65°; analysis calc'd: C 62.18, H 4.17, N 7.25; found: C 62.45, H 4.31, N 6.99.

EXAMPLE 37

4-Fluoro-2-[(1-methyl-2-propynoxyimino)methyl]-phenol mp 43°–44°; analysis calc'd: C 63.76, H 4.86, N 6.76; found: C 63.66, H 4.94, N 6.51.

EXAMPLE 38

2-[(3-Butenoxyimino)methyl]-4-fluorophenol bp 72°–76°/4.7 Pa; analysis calc'd: C 63.15, H 5.78, N 6.69; found: C 63.18, H 5.85, N 6.57.

EXAMPLE 39

4-Fluoro-2-[(3-methylbutoxyimino)methyl]phenol bp 67°–75°/4.7 Pa; analysis calc'd: C 63.98, H 7.16, N 6.22; found: C 64.28, H 6.92, N 6.13.

EXAMPLE 40

2-[(3-Butenoxyimino)methyl]-4,5-dimethylphenol oil; analysis calc'd: C 71.20, H 7.82; found C 71.34, H 8.00.

EXAMPLE 41

2-[(3-Butenoxyimino)methyl]-3-fluorophenol bp 69° C./3 Pa; analysis calc'd: C 65.15, H 5.78; found: C 63.66, H 5.86.

EXAMPLE 42

2-[(3-Butynoxyimino)methyl]-4-chloro-5-methylphenol mp 77.5°–78° C.; analysis calc'd: C 60.64, H 5.09; found: C 59.89, H 5.24.

EXAMPLE 43

2-[(3-Butynoxyimino)methyl]-4-chloro-3-fluorophenol mp 77°–78° C.; analysis calc'd: C 54.71, H 3.76; found: C 54.99, H 3.81.

EXAMPLE 44

2-[(3-Butynoxyimino)methyl]-4 bromo-3-fluorophenol mp 90.5°–91.5° C.; analysis calc'd: C 46.18, H 3.17; found: C 46.83, H 3.36.

EXAMPLE 45

2-[(3-Butynoxyimino)methyl]-4,5-dichlorophenol mp 94°–96° C.; analysis calc'd: C 51.19, H 3.51; found: C 51.50, H 3.40.

EXAMPLE 46

2-[(2-Butynoxyimino)methyl]-4-fluoro-3-methylphenol mp 101°–103° C.; analysis calc'd: C 65.15, H 5.47; found: C 65.13, H 5.20.

EXAMPLE 47

2-[(3-Butynoxyimino)methyl]-4-fluoro 3-methylphenol mp 68°–71° C.; analysis calc'd: C 65.15, H 5.47; found: C 65.35, H 5.36.

EXAMPLE 48

2-[(2-Butynoxyimino)methyl]-4-chloro-3-fluorophenol mp 113°–114° C.; analysis calc'd: C 54.71, H 3.76; found: C 54.93, H 3.77.

EXAMPLE 49

4-Chloro-3-fluoro-2-[(2-propynoxyimino)methyl]-phenol mp 80°–83° C.; analysis calc'd: C 52.76, H 3.10; found: C 52.55, H 2.92.

EXAMPLE 50

4-Chloro-3-fluoro-2[(2-pentynoxyimino)methyl]-phenol mp 84°–85° C.; analysis calc'd: C 56.37, H 4.34; found: C 56.24, H 4.15.

The method of Example 1 was also employed to prepare Compounds A–E, which are outside the scope of the invention, but which are provided for comparison purposes:

A. 4-Bromo-2-[(hydroxyimino)methyl]phenol; mp 127°–128°; analysis calc'd: C 38.92, H 2.80, N 6.48; found: C 38.87, H 2.96, N 6.97.

B. 4-Nitro-2-[(2-propynoxyimino)methyl]phenol; mp 131.5°–133°; analysis calc'd: C 54.55, H 3.66, N 12.72; found: C 54.46, H 3.79, N 12.66.

C. 2-[(Ethoxyimino)methyl]-4-nitrophenol; mp 117.5°–118.5°; analysis calc'd: C 51.43, H 4.80, N 13.33; found: C 51.70, H 4.80, N 13.46.

D. 2-[(Ethoxyimino)methyl]-4-methylphenol; bp 60°/2.7 Pa; analysis calc'd: C 67.02, H 7.31, N 7.82; found: C 67.30, H 7.51, N 7.79.

E. 2-[(Ethoxyimino)methyl]-4-methoxyphenol; mp 33.5°–34°; analysis calc'd: C 61.53, H 6.71, N 7.18; found: C 61.48, H 6.45, N 6.99.

The method of Example 2 was employed to prepare the following compounds in which Q is

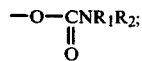

the method of Example 69, using dimethylaminothiocarbamoyl chloride, was employed to obtain the compound of Example 64; the nmr and ir spectra were consistent with the assigned structures:

EXAMPLE 51

5-Chloro-2[N-(2-propynoxyimino)methyl]phenyl methylcarbamate mp 112°–115°; analysis calc'd: C 54.05, H 4.16, N 10.50; found: C 54.22, H 4.16, N 10.72.

EXAMPLE 52

4-Chloro-2-[(2-propenoxyimino)methyl]phenyl methylcarbamate mp 89°–90°; analysis calc'd: C 53.63, H 4.88, N 10.43; found: C 53.64, H 4.96, N 10.62.

EXAMPLE 53

4-Chloro-2-[(propoxyimino)methyl]phenyl methylcarbamate mp 91°–94°; analysis calc'd: C 53.24, H 5.58, N 10.35; found: C 52.94, H 5.64, N 10.64.

EXAMPLE 54

4-Bromo-2-[(2-propynoxyimino)methyl]phenyl methylcarbamate mp 117°–119°; analysis calc'd: C 46.32, H 3.56, N 9.01; found: C 46.59, H 3.52, N 8.72.

EXAMPLE 55

4-Chloro-2-[(methoxyimino)methyl]phenyl methylcarbamate mp 125°–126°; analysis calc'd: C 49.50, H 4.57, N 11.54; found: C 49.64, H 4.72, N 11.74.

EXAMPLE 56

4-Chloro-2-[(ethoxyimino)methyl]phenyl methylcarbamate mp 120°–121°; analysis calc'd: C 51.47, H 5.11, N 10.91; found: C 50.95, H 4.98, N 10.91.

EXAMPLE 57

4-Bromo-2-[(methoxyimino)methyl]phenyl methylcarbamate mp 130°–131.5°; analysis calc'd: C 41.83, H 3.86, N 9.76; found: C 41.70, H 4.00, N 9.49.

EXAMPLE 58

4-Bromo-2-[(ethoxyimino)methyl]phenyl methylcarbamate mp 112°–114°; analysis calc'd: C 43.87, H 4.35, N 9.30; found: C 44.85, H 4.47, N 9.23.

EXAMPLE 59

4-Bromo-2-[(propoxyimino)methyl]phenyl methylcarbamate mp 106°–107°; analysis calc'd: C 45.73, H 4.79, N 8.89; found: C 45.95, H 4.59, N 8.67.

EXAMPLE 60

4-Bromo-2-[(butoxyimino)methyl]phenyl methylcarbamate mp 91°–92°; analysis calc'd: C 47.43, H 5.21, N 8.51; found: C 47.25, H 5.11, N 8.65.

EXAMPLE 61

2-[(Butoxyimino)methyl]-4-chlorophenyl methylcarbamate mp 77°–78°; analysis calc'd: C 54.84, H 6.02, N 9.84; found: C 54.84, H 6.15, N 9.87.

EXAMPLE 62

4-Chloro-2-[(ethoxyimino)methyl]phenyl propylcarbamate mp 75°–76°; analysis calc'd: C 54.83, H 6.02, N 9.84; found: C 54.56, H 5.73, N 10.12.

EXAMPLE 63

4-Chloro-2-[(ethoxyimino)methyl]phenyl butylcarbamate mp 93°–94°; analysis calc'd: C 56.28, H 6.41, N 9.38; found: C 56.36, H 6.52, N 9.50.

EXAMPLE 64

2-[(Methoxyimino)methyl]phenyl dimethylthiocarbamate mp 73°–74°; analysis calc'd: C 55.44, H 5.92, N 11.75; found: C 55.30, H 5.88, N 11.79.

The method of Example 2 was also employed to prepare compounds F–J, some of which are outside the scope of the invention, but which are provided for comparison purposes:

F. 4-Methyl-2-[(2-propynoxyimino)methyl]phenyl methylcarbamate; mp 83.5°–84°; analysis calc'd: C 63.40, H 5.73, N 11.37; found: C 63.12, H 5.78, N 11.38.

G. 5-Methyl-2-[(2-propynoxyimino)methyl]phenyl methylcarbamate; mp 85°–88°; analysis calc'd: C 63.40, H 5.73, N 11.37; found: C 63.21, H 5.76, N 11.31.

H. 6-Nitro-2-[(2-propynoxyimino)methyl]phenyl methylcarbamate; mp 118°–120°; analysis calc'd: C 51.99, H 4.00, N 15.16; found: C 51.90, H 4.02, N 15.42.

I. 4,6-Dichloro-2-[(2-propynoxyimino)methyl]phenyl methylcarbamate; mp 129°–131°; analysis calc'd: C 47.86, H 3.35, N 9.30; found: C 47.65; H 3.32, N 9.01.

J. 4,6-Dibromo-2-[(2-propynoxyimino)methyl]phenyl methylcarbamate; mp 139°–139.5°; analysis calc'd: C 36.95, H 2.58, N 7.18; found: C 37.07, H 2.51, N 7.16.

The method of Example 3 was employed to prepare the following compounds in which Q is

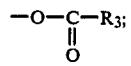

the nmr and ir spectra were consistent with the assigned structure:

EXAMPLE 65

4-Chloro-2-[(2-propynoxyimino)methyl]phenyl acetate mp 70.5°–71.5°; analysis calc'd: C 57.27, H 4.01, N 5.57; found: C 58.38, H 4.20, N 5.49.

EXAMPLE 66

4-Chloro-2-[(methoxyimino)methyl]phenyl acetate mp 42.5°–44°; analysis calc'd: C 52.76, H 4.43, N 6.15; found: C 53.05, H 4.38, N 5.86.

EXAMPLE 67

2-[(Butoxyimino)methyl]-4-fluorophenyl acetate bp 95.5°/3 Pa; analysis calc'd: C 61.65, H 6.37, N 5.53; found: C 61.68, H 6.55, N 5.57.

EXAMPLE 68

2-[(Cyclopropylmethoxyimino)methyl]-4-fluorophenyl acetate bp 100°–104°/3Pa; analysis calc'd: C 62.14, H 5.62, N 5.57; found C 62.00, H 5.68, N 5.18.

EXAMPLE 69

4-Chloro-2-[(2-propynoxyimino)methyl]phenyl 2,2-dimethylpropanoate

To a stirred solution of 2.9 grams (0.014 mole) of 4-chloro-2-[(2-propynoxyimino)methyl]phenol (Example 1 product) in 25 ml of toluene was added 1.4 grams (0.014 mole) of triethylamine followed by 1.8 grams (0.015 mole) of trimethylacetyl chloride, both in one portion. A solid formed upon addition of the acid chloride. A catalytic amount (0.1 gram) of 4-dimethylaminopyridine was added and the reaction mixture was stirred at ambient temperature for 16 hours, heated for five hours, then allowed to cool to ambient temperature where it was stirred for 60 hours. The reaction mixture was poured into a separatory funnel with 150 ml of toluene and 25 ml of ethyl acetate. Water was added until all solids were dissolved. The mixture was shaken and the aqueous layer removed. The organic layer was washed with three portions of 20 ml each of aqueous 1 N hydrochloric acid, three portions of 25 ml each of water, and finally, 25 ml of an aqueous solution saturated with sodium chloride. The organic layer was dried with sodium sulfate and filtered. The filtrate was concentrated under reduced pressure to give a residual oil. The oil was distilled under reduced pressure to give 2.2 grams of 4-chloro-2-[(2-propynoxyimino)methyl]phenyl 2,2-dimethylpropanoate; b.p. 114°–117°/0.8 Pa.

The nmr and ir spectra were consistent with the assigned structure.

Analysis calc'd for $C_{15}H_{16}ClNO_3$: C61.33:H5.49:N4.77; Found: C 60.54; H 5.60; N 4.82.

The method of Example 69 was employed to prepare the following compounds in which Q is -O-C-R₃; the nmr and ir spectra were consistent with the assigned structure.

EXAMPLE 70

4-Chloro-2-[(2-propynoxyimino)methyl]phenyl 4-nitrobenzoate; mp 118°–119°; analysis calc'd: C 56.92, H 3.09, N 7.81; found: C 57.02, H 3.30, N 7.75.

EXAMPLE 71

4-Chloro-2-[(2-propynoxyimino)methyl]phenyl 4-methoxybenzoate;

mp 118°–120°; analysis calc'd: C 62.89, H 4.11, N 4.07; found: C 61.81, H 4.50, N 3.75.

EXAMPLE 72

4-Chloro-2-[(2-propynoxyimino)methyl]phenyl 2-chloroacetate mp 78°–80°; analysis calc'd: C 50.37, H 3.17, N 4.89; found: C 50.22, H 3.42, N 5.01.

EXAMPLE 73

4-Chloro-2-[(2-propynoxyimino)methyl]phenyl 2,2,2-trichloroacetate liquid; analysis calc'd: C 40.59, H 1.99, N 3.95; found: C 40.89, H 2.02, N 3.99.

EXAMPLE 74

4-Chloro-2-[(2-propynoxyimino)methyl]phenyl 4-methyl-4-nitropentanoate mp 60°–62°; analysis calc'd: C 54.48, H 4.86, N 7.94; found: C 54.34, H 5.10, N 8.04.

A compound in which Q is $-OSiR_4R_5R_6$ was prepared by reaction of a trialkyl silyl chloride with the compound of Example 1 in dimethylformamide, using imidazole as acid acceptor; the nmr and ir spectra were consistent with the assigned structure:

EXAMPLE 75

4-Chloro-2-[dimethyl-(1,1-dimethylethyl)silyloxy]-N-(2-propynoxy)benzaldimine bp 100°–105°/2.7 Pa; analysis calc'd: C 59.33, H 6.85, N 4.32; found: C 59.04, H 6.55, N 4.66.

Biological Testing

The compounds of Examples 1–75 were formulated and tested for nematicidal activity as formulated materials. The formulation used was a standard 5 weight percent dust formu-lation made up as follows:

| | |
|---|---|
| Active ingredient (100% active basis) | 5 parts |
| Base | 95 parts |
| 96% attapulgite clay | |
| 2% highly purified sodium lignosulfonate (100%) | |
| 2% powdered sodium alkylnaphthalenesulfonate (75%); | | the mixture was ground to a fine powder.

The formulations described above were tested for activity against root-knot nematode (*Meloidogyne incognita*) as follows:

Nematode Culture—Tomato seedlings with two large true leaves were transplanted into six inch clay pots containing steam-sterilized sandy soil. One week after transplanting, galled roots of nematode-infested tomato plants, with fully developed egg masses, were placed in three holes in the soil around the seedling roots. Holes were then closed with soil. The plants were allowed to grow until fully developed egg masses were formed (6 to 7 weeks after inoculation).

Inoculum Preparation—Infected tomato roots, containing egg masses, were cleaned under running tap water, cut into short pieces and comminuted with water in an electrical blender for 30 seconds. The shredded roots were poured onto layers of washed sand in a wooden flat. The flat was covered with plastic sheeting and kept at greenhouse temperatures for 3 to 7 days to allow about 50% of the larvae to hatch.

Preparation of Root-Knot Nematode Infested Soil—Samples of the infested soil prepared as described above were processed for nematodes by using the Caveness and Jensen centrifugal-sugar flotation extraction technique [Caveness, F.E. and Jensen, H.J., "Modification of the Centrifugal Flotation Technique for the Isolation and Concentration of Nematodes and their Eggs from Soil and Plant Tissue", Proc. Helm. Soc., Washington, 22, 87-89 (1955).]

Fine wire cloth screen (No. 500, U.S.A. Standard Sieve Series) was used to collect the nematodes and eggs, and their number was estimated under a stereomicroscope. Enough sand containing eggs and larvae was mixed with additional steam-sterilized sandy soil so that there were 600 to 800 root-knot nematode larvae and eggs per pot of soil (three inch diameter each, containing approximately 300 g soil). Depending on the total amount of nematode infested soil needed, mixing was accomplished by use of a cement mixer for 5 minutes or a V-shaped rotary mixer for 60 seconds.

Soil so infected was used for soil incorporated nematicidal studies within 2 days of preparation. The formulated compounds to be tested for nematicidal activity were incorporated in the root-knot nematode infested potting soil to give soil treatment at a rate of 25 ppm, 10 ppm, and 5 ppm (weight chemical/volume soil). Young tomato plants were planted in this soil in three-inch pots. Untreated check plants were treated in the same manner as those treated with the active ingredient. The formulation base, without active ingredient, was added to the soil for untreated plants and separate untreated plants were used to detect the effects, if any, of chemicals in the formulation base. Each test series also included a formulation of carbofuran, a known nematicide, as a standard for comparison.

At the end of two weeks the roots of all plants were examined and rated in comparison to untreated checks, using the following system:

Knot Index

4 —No control—amount of swellings equivalent to that developed on the roots of the untreated check plants.
3 —Amount of swellings 25% less than that developed on the roots of the untreated check plants.
2 —Amount of swellings 50% less than that developed on the roots of the untreated check plants.
1 —Amount of swellings 75% less than that developed on the roots of the untreated check plants.
0 —No swellings—complete control.

When the control observed is between 1 and 0 the Knot Index is subdivided to indicate how close the control is to 75% or to 100%. For this subdivision numbers between 0 and 1 are used as follows:

| | |
|---|---|
| 0.8 | 80% control |
| 0.5 | 90% control |
| 0.4–0.1 | 95–99% control |

The knot index for the untreated check was 4.0. Results for the compositions of the invention and for compositions with Comparison Compounds A to J are recorded in Table I.

Evaluation of compositions of the invention against stunt nematode (*Tylenchorhynchus claytoni*) was carried out by incorporating the formulated active ingredient in soil in which a corn seedling was then planted, and two days thereafter inoculating the soil with stunt nematode larvae. The soil was processed for nematode counting approximately five weeks after treatment. Untreated check plants showed no nematode control. Results with formulations of active ingredients of the invention and carbofuran formulations are recorded in Table II as "Percent Control" relative to nematode control in the untreated check pot. The active ingredients tested showed control ranging from 38% to 99%; several compounds gave better nematode control than carbofuran in direct comparisons.

Compositions were also evaluated against lesion nematode (*Pratylenchus penetrans*), following a similar procedure in which pea seedlings were planted instead of corn seedlings, and nematodes were extracted from the root systems, instead of from the soil. Untreated plants showed no nematode control. Results with formulations of active ingredients of the invention and with carbofuran formulations are recorded in Table III. Activity was generally lower than that observed against stunt nematodes, but 26 of 29 compounds tested showed control of lesion nematodes, ranging from 5% to 100%.

Various modifications may be made in the formulation and application of the novel compositions of this invention without departing from the inventive concept herein, as defined in the claims below.

TABLE I

Activity Against Root Knot Nematodes of Salicyaldehyde Derivatives Soil Incorporated as 5% Dust at 25, 10, 5 ppm

| Compound of Example | Knot Index[1], Average[2] | | |
|---|---|---|---|
| | 25 ppm | 10 ppm | 5 ppm |
| 1 | 0 | 0 | .04 |
| 2 | .12 | .43 | 1.2 |
| 3 | 0 | .12 | — |
| 4 | 3.0 | — | — |
| 5 | 0 | .10 | 4.0 |
| 6 | 0 | 0 | 0 |
| 7 | 0 | .11 | 1.1 |
| 8 | 0 | .78 | 3.0 |
| 9 | 0 | .07 | .29 |
| 10 | 0 | .19 | .36 |
| 11 | 0 | .19 | .88 |
| 12 | 0 | .35 | .79 |
| 13 | 0 | 1.7 | 4.0 |
| 14 | 0 | 0 | .35 |
| 15 | 0 | .19 | .51 |
| 16 | 0 | .12 | .95 |
| 17 | 0 | .95 | 3.0 |
| 18 | .57 | .95 | 4.0 |
| 19 | 0 | .45 | 2.0 |
| 20 | 0 | .32 | 0 |
| 21 | 4.0 | — | — |
| 22 | .25 | 2.0 | — |
| 23 | 0 | 0 | — |
| 24 | — | 1.45 | 3.0 |
| 25 | — | 1.0 | 2.75 |
| 26 | — | 1.5 | 4.0 |
| 27 | 0 | .25 | 2.5 |
| 28 | — | .20 | 4.0 |
| 29 | 0 | 0 | 0 |
| 30 | — | 0 | 0 |
| 31 | 0 | 0 | .70 |
| 32 | — | .40 | 1.0 |
| 33 | .50 | 4.0 | 4.0 |
| 34 | 0 | 0 | 0 |
| 35 | 0 | 0 | .40 |
| 36 | .40 | 1.2 | 4.0 |
| 37 | 1.0 | 3.5 | 4.0 |
| 38 | 0 | 0 | 0 |
| 39 | 0 | .25 | .13 |
| 40 | 0 | .53 | — |
| 41 | 0 | 0 | .75 |
| 42 | 0 | 0 | 0 |
| 43 | 0 | 0 | 0 |
| 44 | 0 | 0 | — |
| 45 | .05 | .83 | 1.75 |
| 46 | 0 | .17 | .17 |
| 47 | 0 | .27 | 1.0 |

TABLE I-continued

Activity Against Root Knot Nematodes of Salicyaldehyde Derivatives Soil Incorporated as 5% Dust at 25, 10, 5 ppm

| | Knot Index[1], Average[2] | | |
|---|---|---|---|
| | 25 ppm | 10 ppm | 5 ppm |
| 48 | 0 | .05 | .50 |
| 49 | 0 | 0 | 0 |
| 50 | 0 | .05 | .82 |
| 51 | 4.0 | — | — |
| 52 | 0 | .40 | 1.5 |
| 53 | 0 | .87 | 3.3 |
| 54 | .25 | 1.0 | 3.3 |
| 55 | .53 | .78 | 3.0 |
| 56 | 0 | 1.5 | 4.0 |
| 57 | .06 | .98 | 4.0 |
| 58 | 1.0 | 4.0 | — |
| 59 | .61 | 1.35 | 3.7 |
| 60 | 4.0 | 4.0 | — |
| 61 | 1.8 | 4.0 | — |
| 62 | .50 | 1.2 | 3.7 |
| 63 | 4.0 | 4.0 | — |
| 64 | .90 | 2.3 | 3.0 |
| 65 | 0 | 0 | .12 |
| 66 | — | .20 | .50 |
| 67 | 0 | 0 | .10 |
| 68 | 0 | 0 | 1.2 |
| 69 | 0 | 0 | .25 |
| 70 | .50 | 1.0 | 2.8 |
| 71 | 1.2 | 3.0 | 3.7 |
| 72 | 0 | 0 | 0 |
| 73 | 0 | 0 | 1.5 |
| 74 | 0 | 0 | 0 |
| 75 | 0 | .12 | 2.0 |
| Comparison Compounds | | | |
| A | 4.0 | — | — |
| B | 4.0 | — | — |
| C | 4.0 | — | — |
| D | 4.0 | — | — |
| E | 4.0 | — | — |
| F | 4.0 | — | — |
| G | 4.0 | — | — |
| H | 4.0 | — | — |
| I | 4.0 | 4.0 | 4.0 |
| J | 4.0 | 4.0 | 4.0 |

[1]Explanation of Knot Index in text.
[2]Average of four replicates. Untreated check plants showed no nematode control (Knot Index = 4.0).

TABLE II

Activity Against Stunt Nematodes of Salicyaldehyde Derivatives Soil Incorporated as 5% Dust at 20, 15, 10 ppm

| Compound of Example | Percent Control[1,2] | | | Carbofuran | |
|---|---|---|---|---|---|
| | 20 ppm | 15 ppm | 10 ppm | 10 ppm | 15 ppm |
| 1 | 89 | — | — | 73 | — |
| 3 | — | — | 48 | 67 | — |
| 5 | 94 | — | — | 73 | — |
| 6 | — | — | 74 | 78 | — |
| 7 | 83 | — | — | 73 | — |
| 8 | 88 | — | — | 73 | — |
| 9 | 94 | — | — | 75 | — |
| 9 | — | — | 60 | 79 | — |
| 10 | — | — | 59 | 66 | — |
| 11 | — | — | 62 | 66 | — |
| 12 | — | — | 46 | 66 | — |
| 14 | — | — | 60 | 66 | — |
| 15 | — | — | 38 | 66 | — |
| 16 | — | — | 74 | 78 | — |
| 17 | — | — | 70 | 78 | — |
| 18 | — | — | 99 | 78 | — |
| 19 | — | — | 62 | 78 | — |
| 20 | — | — | 44 | 77 | — |
| 28 | — | 69 | — | — | 70 |
| 30 | — | 94 | — | — | 70 |
| 32 | — | 78 | — | — | 70 |
| 40 | — | 74 | — | — | — |
| 41 | — | 70 | — | — | — |
| 42 | — | 97 | — | — | — |
| 44 | — | 47 | — | — | — |
| 52 | 89 | — | — | 63 | — |
| 53 | 80 | — | — | 63 | — |
| 54 | 70 | — | — | 63 | — |
| 55 | 58 | — | — | 73 | — |
| 57 | 56 | — | — | 66 | — |
| 66 | — | 53 | — | — | 70 |

[1]Average of 3-4 replicates. Untreated check showed no control.
[2]Percent control is $$\frac{\left(\begin{array}{c}\text{Average Nematode}\\\text{Count in Check}\end{array}\right) - \left(\begin{array}{c}\text{Average Nematode}\\\text{Count in Treated Soil}\end{array}\right)}{\left(\begin{array}{c}\text{Average Nematode}\\\text{Count in Check}\end{array}\right)} \times 100$$

TABLE III

Activity Against Lesion Nematodes of Salicyaldehyde Derivatives Soil Incorporated as 5% Dust at 20, 15, 10 ppm

| Compound of Example | Percent Control[1,2] | | | Carbofuran | |
|---|---|---|---|---|---|
| | 20 ppm | 15 ppm | 10 ppm | 10 ppm | 15 ppm |
| 1 | 72 | — | — | 71 | — |
| 3 | — | — | 23 | 85 | — |
| 5 | 63 | — | — | 66 | — |
| 6 | — | — | 30 | 92 | — |
| 7 | 44 | — | — | 66 | — |
| 8 | 48 | — | — | 66 | — |
| 9 | 45 | — | — | 77 | — |
| 9 | — | — | 68 | 94 | — |
| 10 | — | — | 71 | 90 | — |
| 11 | — | — | 0 | 90 | — |
| 12 | — | — | 34 | 90 | — |
| 14 | — | — | 17 | 90 | — |
| 15 | — | — | 44 | 90 | — |
| 16 | — | — | 24 | 92 | — |
| 17 | — | — | 46 | 92 | — |
| 18 | — | — | 100 | 92 | — |
| 19 | — | — | 22 | 92 | — |
| 28 | — | 41 | — | — | 95 |
| 30 | — | 49 | — | — | 95 |
| 32 | — | 30 | — | — | 95 |
| 40 | — | 37 | — | — | — |
| 41 | — | 0 | — | — | — |
| 42 | — | 0 | — | — | — |
| 43 | — | 46 | — | — | — |
| 52 | 62 | — | — | 63 | — |
| 53 | 65 | — | — | 63 | — |
| 54 | 43 | — | — | 63 | — |
| 55 | 53 | — | — | 66 | — |
| 57 | 5 | — | — | 81 | — |
| 66 | — | 46 | — | — | 95 |

[1]Average of 3-4 replicates. Untreated check showed no control.
[2]Percent control is $$\frac{\left(\dfrac{\text{Nematode Count in Check}}{\text{Root Weight in Check}}\right) - \left(\begin{array}{c}\text{Nematode Count}\\\text{in Treatment}\\\hline\text{Root Weight}\\\text{in Treatment}\end{array}\right)}{\left(\dfrac{\text{Nematode Count in Check}}{\text{Root Weight in Check}}\right)} \times 100$$

We claim:

1. A method for the control of soil nematodes by applying to the situs of infestation a nematicidally effective amount of a composition comprising as active ingredient in admixture with a solid extender a compound of the formula:

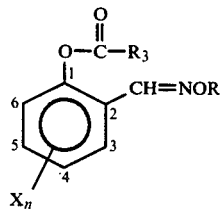

wherein

R is $C_2$–$C_4$ alkyl, 2-propynyl, cyclopropylmethyl;

$R_3$ is $C_1$–$C_6$ alkyl, straight or branched, optionally substituted with chlorine or nitro;

X is fluorine, chlorine in the 4-position;

n is 1.

2. The method of claim 1 in which the active ingredient is 4-chloro-2-[(propoxyimino)methyl]phenyl acetate.

3. The method of claim 1 in which the active ingredient is 4-chloro-2-[(2-propynoxyimino)methyl]phenyl acetate.

4. The method of claim 1 in which the active ingredient is 4-chloro-2-[(2-propynoxyimino)methyl]phenyl 2,2-dimethylpropanoate.

5. The method of claim 1 in which the active ingredient is 2-[(butoxyimino)methyl]-4-fluorophenyl acetate.

6. The method of claim 1 in which the active ingredient is 2-[(cyclopropylmethyloxyimino)methyl]-4-fluorophenyl acetate.

7. The method of claim 1 in which the active ingredient is 4-chloro-2-[(2-propynoxyimino)methyl]phenyl 2-chloroacetate.

8. The method of claim 1 in which the active ingredient is 4-chloro-2-[(2-propynoxyimino)methyl]phenyl 2,2,2-trichloroacetate.

9. The method of claim 1 in which the active ingredient is 4-chloro-2-[(2-propynoxyimino)methyl]phenyl 4-methyl-4-nitropentanoate.

10. A compound of the formula:

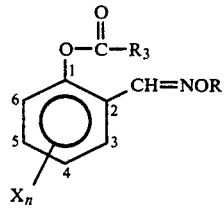

wherein

R is 2-propynyl;

$R_3$ is $C_1$–$C_6$ alkyl, straight or branched, substituted with at least one chlorine or nitro group;

X is fluorine, chlorine in the 4-position;

n is 1.

11. The compound of claim 2 which is 4-chloro-2-[(2-propynoxyimino)methyl]phenyl 2-chloroacetate.

12. The compound of claim 2 which is 4-chloro-2-[(2-propynoxyimino)methyl]phenyl 2,2,2-trichloroacetate.

13. The compound of claim 2 which is 4-chloro-2-[(2-propynoxyimino)methyl]phenyl 4-methyl-4-nitropentanoate.

* * * * *